United States Patent [19]

Connelly

[11] Patent Number: 5,255,976
[45] Date of Patent: Oct. 26, 1993

[54] TEMPERATURE GRADIENT CALORIMETER

[75] Inventor: Patrick R. Connelly, Groton, Mass.

[73] Assignee: Vertex Pharmaceuticals Incorporated, Cambridge, Mass.

[21] Appl. No.: 911,592

[22] Filed: Jul. 10, 1992

[51] Int. Cl.$^5$ .......................................... G01K 17/00
[52] U.S. Cl. ...................................... 374/31; 422/99; 422/51
[58] Field of Search .................... 422/51, 68.1, 99; 374/31, 33, 36, 37, 43, 44, 112, 10, 11, 30; 250/361 C

[56] References Cited

U.S. PATENT DOCUMENTS

| | | | |
|---|---|---|---|
| 3,417,604 | 12/1968 | Bean et al. | 374/11 |
| 3,789,662 | 2/1974 | Zettler et al. | 374/31 |
| 4,126,032 | 11/1978 | Ikeda et al. | 374/10 |
| 4,151,252 | 4/1979 | Marchand et al. | 422/51 |
| 4,284,725 | 8/1981 | Fennel, III et al. | 422/99 |
| 4,325,910 | 4/1982 | Jordan | 422/99 |
| 4,495,149 | 1/1985 | Iwata et al. | 422/99 |
| 4,858,155 | 8/1989 | Okawa et al. | 374/31 |
| 4,874,250 | 10/1989 | Gönner | 374/43 |
| 5,030,012 | 7/1991 | Hagins et al. | 374/31 |
| 5,149,505 | 9/1992 | English et al. | 422/99 |

OTHER PUBLICATIONS

Dynatech Laboratories, Inc. brochure "Buy A Microplate Reader With More In Mind" (no date).
W. Selove, et al., *Nuclear Instruments and Methods*, 161, No. 2: 233-242 (1979).

*Primary Examiner*—William A. Cuchlinski, Jr.
*Assistant Examiner*—G. Bradley Bennett
*Attorney, Agent, or Firm*—James F. Haley, Jr.; Margaret A. Pierri; Kevin E. Flynn

[57] ABSTRACT

A temperature gradient calorimeter and method of calculating heats of reactions is disclosed. The calorimeter has a two dimensional array of reaction chambers located in a thermally conductive substrate. A first heat transfer medium is in thermal contact with the thermal conductive substrate and is located at one region of the array of reaction chambers. A second heat transfer medium is in thermal contact with the thermal conductive substrate and is located on the opposite side of the array from the first heat transfer medium. The first and second heat transfer mediums are at two different temperatures. That temperature difference produces a temperature gradient across the array of reaction chambers.

The fluorescence intensities are measured for reactant samples located in the array of reaction chambers. By inserting the fluorescence intensity data into thermodynamic equations expressing the degree of advancement and the heat of reaction, the heat of reaction for the reaction process of the sample can be determined.

24 Claims, 6 Drawing Sheets

| | 1 | 2 | 3 | 4 | 5 | 6 | 7 | 8 | 9 | 10 | 11 | 12 |
|---|---|---|---|---|---|---|---|---|---|---|---|---|
| a | 98 | 95 | 93 | 90 | 74 | 51 | 23 | 8.1 | 0.9 | 0.5 | 0.1 | 0.0 |
| b | 98 | 98 | 97 | 96 | 94 | 92 | 78 | 55 | 21 | 4 | 0.4 | 0.1 |
| c | 99 | 92 | 84 | 72 | 61 | 45 | 21 | 10 | 4.0 | 3.0 | 0.4 | 0.1 |
| d | 99 | 92 | 84 | 72 | 61 | 45 | 21 | 10 | 4.0 | 3.0 | 0.4 | 0.1 |
| e | 99 | 99 | 99 | 82 | 51 | 45 | 23 | 4.0 | 1 | 0.1 | 0.4 | 0.1 |
| f | 111 | 92 | 87 | 62 | 61 | 44 | 11 | 10 | 4.0 | 3.3 | 0.1 | 0.1 |
| g | 112 | 82 | 94 | 72 | 60 | 47 | 31 | 19 | 4.9 | 3.0 | 0.1 | 0.0 |
| h | 121 | 99 | 94 | 62 | 61 | 35 | 21 | 19 | 17 | 7 | 4 | 1.0 |

ROWS / COLUMNS

NUMBERS IN BOXES REPRESENT FLUORESCENCE INTENSITY

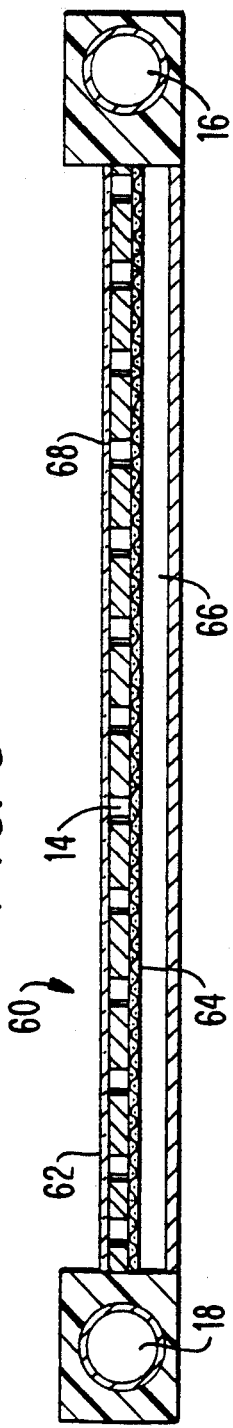
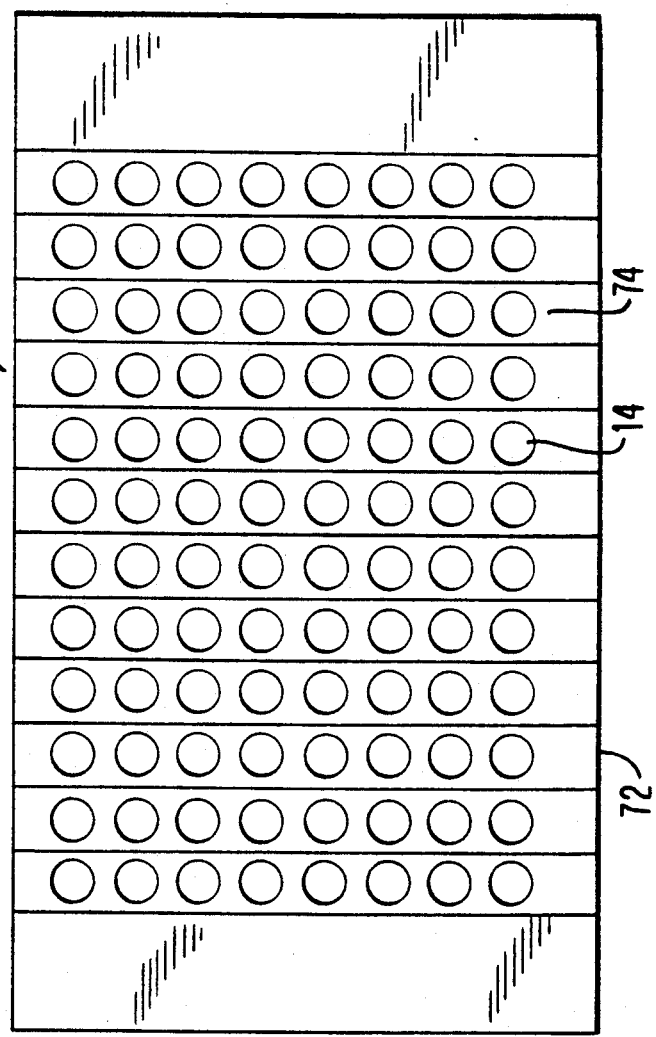

TEMPERATURE GRADIENT CALORIMETER

BACKGROUND OF THE INVENTION

Biological calorimetry is a field primarily concerned with the measurement of the heat effects produced in biochemical processes. There are two categories of reaction processes of interest which produce heat while reacting.

The first category of reactions are those between two chemical entities (reactants M and X) to produce a third species (product MX), such as the binding of a drug to a protein molecule to produce a drug/protein complex. This binding (intermolecular) reaction is depicted by the chemical reaction equation, $M+X \rightarrow MX$.

The second category of reactions are those that result in a transformation of the molecular state of a substance (from the reactant state M to the product state M') due to an increase in temperature, such as the unfolding of proteins and various nucleic acid structures or the melting of a lipid suspension. This unfolding (intramolecular) reaction is depicted by the chemical reaction equation, $M \rightarrow M'$.

Typically, one measures the heat effects for binding (intermolecular) reactions (i.e. the first category) using a conventional calorimeter by mixing the reactants in a "reaction chamber" while monitoring the temperature change in the reaction chamber with a thermometer or a thermoelectric sensor. The temperature or voltage change is converted into a unit of heat by calibrating the calorimeter against a standard heat effect generated by the passage of electric current through a resistor placed in the reaction chamber.

Similarly, one typically measures the heat effect due to unfolding (intramolecular) reactions (i.e. the second category) using a scanning calorimeter, which measures the heat effect produced upon increasing the temperature of the contents of a reaction chamber.

Conventional methods of thermodynamic data collection for chemical reactions tend to be very repetitive and time consuming. Using conventional methods, the time required to determine the equilibrium constant and enthalpy of the unfolding of a protein at eight different values of PH can take between 3 to 8 days. Another limitation of conventional methods is that two different devices are needed to measure both binding (intermolecular) and unfolding (intramolecular) reactions. In addition, the accuracy of a conventional reaction calorimeter is limited by heat effects caused by stirring the reactants in the reaction chamber. The use of conventional scanning calorimeters can be very time consuming because scanning calorimeters tend to require lengthy temperature equilibrium periods.

Therefore, a need exists for a single device which can determine heat effects for both binding (intermolecular) and unfolding (intramolecular) reactions with increased accuracy and in less time than traditional methods.

SUMMARY OF THE INVENTION

The present invention provides a temperature gradient calorimeter with two dimensional data collection capability for monitoring both type binding (intermolecular) and unfolding (intramolecular) reactions involving temperature changes with increased accuracy and which significantly reduces the amount of time required for determining heat effects of chemical reactions from traditional methods. The temperature gradient calorimeter of the invention determines heats of reactions by correlating reaction processes with differences in patterns of radiation intensity changes (fluorescence preferred) that occur due to a fixed temperature differential.

The calorimeter apparatus in general is comprised of wells forming a two dimensional array of reaction chambers disposed in a thermally conductive substrate. A preferred array is a horizontal row and vertical column arrangement forming an x-y array where each row in the x-direction has twelve wells and where each column in the y-direction has eight wells. A first heat transfer medium at a first temperature $T_1$ is in thermal contact with the thermally conductive substrate at a first region of the substrate. A second heat transfer medium at a different temperature $T_2$ is in thermal contact with the thermally conductive substrate at a second region. The difference in temperatures between the first and second heat transfer mediums produces a fixed and highly stable temperature gradient $T_1-T_2$ along the x-axis across the array of reaction chambers disposed between the two regions.

The array of reaction chambers are filled with a measured amount of premixed reactant solution. An x-y array would for example, have a different pH in each row resulting in a variance of reaction conditions in the y-axis. The fluorescence intensity in each reaction chamber is measured with a sensoring device and converted to digitized data. The result is the collection of fluorescence intensity data which provides a fluorescence profile of the extent of reaction (degree of advancement) across the temperature gradient. The digitized fluorescence profile data is then processed in a computer which compares the data to stored data concerning known relationships between the degree of advancement of reaction and heat of reaction for known parameters, to determine the heat of reaction and equilibrium constant for the reaction process under consideration.

BRIEF DESCRIPTION OF THE DRAWINGS

The foregoing and other objects, features and advantages of the invention will be apparent from the following more particular description of preferred embodiments of the drawings in which like reference characters refer to the same parts throughout the different views. The drawings are not necessarily to scale, emphasis instead being placed upon illustrating the principles of the invention.

FIG. 8 is a section end view of the present invention having an environment chamber.

FIG. 9 is a plan view of a segmented temperature gradient calorimeter.

DETAILED DESCRIPTION OF THE PREFERRED EMBODIMENT

Figure 1:
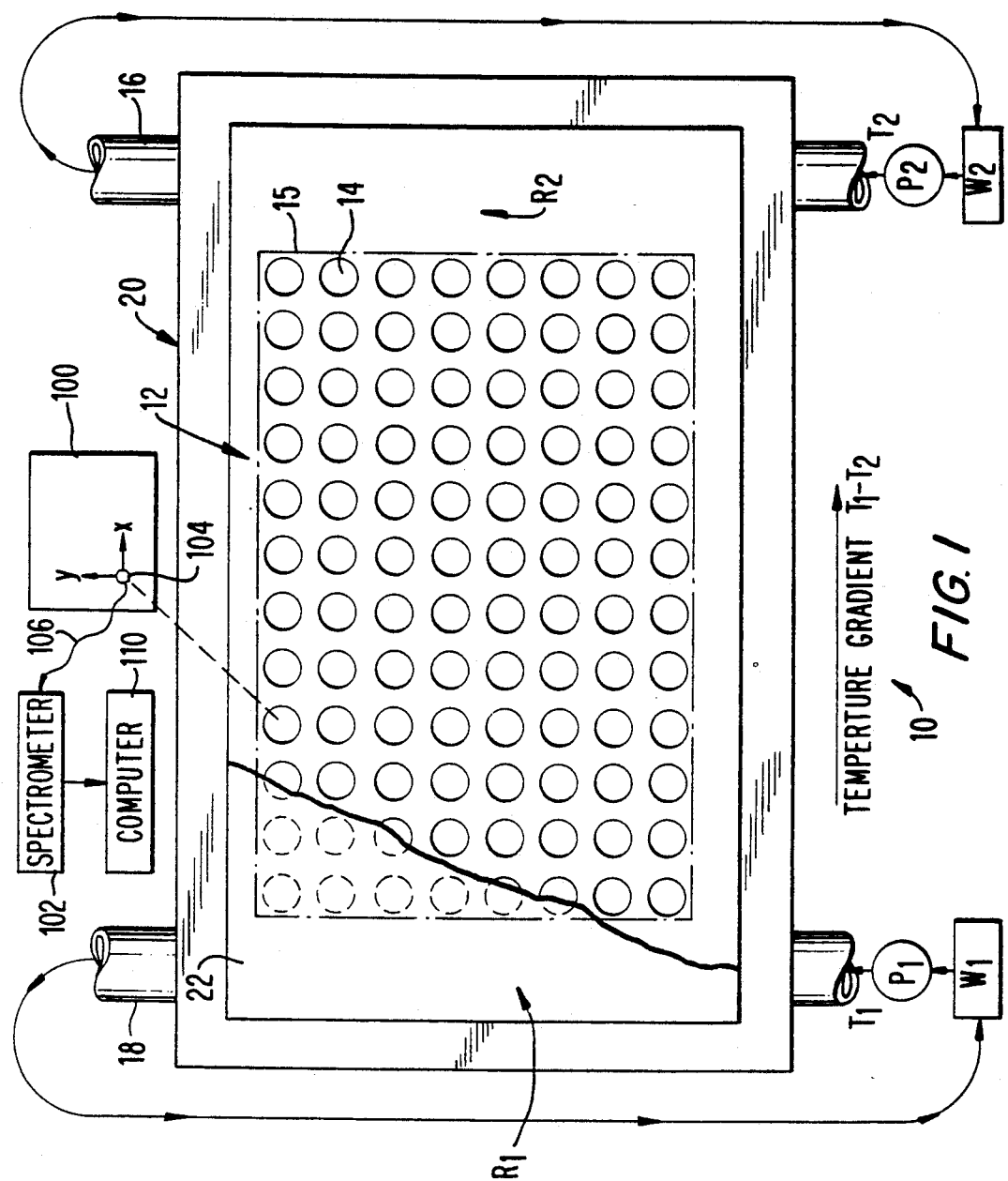
FIG. 1 is a plan view of the present invention temperature gradient calorimeter.
Figure 2:
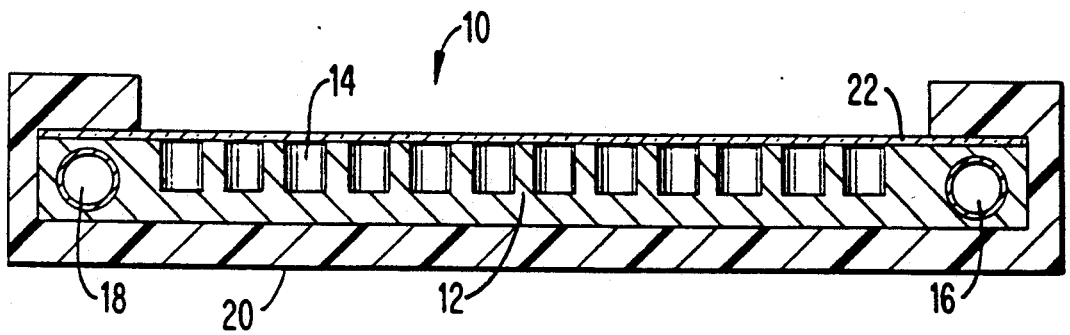
FIG. 2 is a section end view of the present invention temperature gradient calorimeter.

In FIGS. 1 and 2, an x-y array 15 (wherein x=12, y=8) of wells 14 are formed, such as by drilling holes into a substrate 12 to form temperature gradient calorimeter 10. In a preferred embodiment, substrate 12 is a plate formed from a 6"×3.5"×0.5" block of copper. Alternatively substrate 12 can be of various dimensions or shapes and can be made of other thermally conductive materials such as saphire, silicon, aluminum or stainless steel.

Flow tube 18 is located at one edge of the array of wells 14 and passes through substrate 12 along region $R_1$. Circulating pump $P_1$ circulates water from water bath $W_1$ through flow tube 18. Water bath $W_1$ is held at a constant temperature $T_1$ by a heating coil (not shown). Alternatively, a cooling coil may be used to maintain a constant temperature in water bath $W_1$. Copper tube 16 is located at an opposite edge of the array and passes through reaction plate 12 along region $R_2$. Circulating pump $P_2$ circulates water from water bath $W_2$ through flow tube 16. Water bath $W_2$ is held at a constant temperature $T_2$ in similar fashion as water bath $W_1$. The temperatures $T_1$ and $T_2$ can range anywhere between 0° C. to 100° C. In the preferred embodiment, flow tubes 16 and 18 are made of copper. Alternatively, flow tubes 16 and 18 may be made of any thermally conductive material such as aluminum and stainless steel. The difference in temperature between flow tube 18 and flow tube 16 produces a fixed and highly stable temperature gradient $T_1 - T_2$ across substrate 12 and array 15.

In FIGS. 1 and 2, insulation 20 is provided to insulate substrate 12, substantially isolating calorimeter 10 from the ambient temperature surrounding calorimeter 10. Insulation 20 may be formed of Styrofoam ™ or any other material with good insulating properties can be used. Quartz window 22 is also provided to cover the upper surface of substrate 12 thereby covering wells 14. Additionally, quartz window 22 also serves to isolate wells 14 from the surrounding ambient temperature. Alternatively, window 22 can be made of other transparent materials. By isolating calorimeter 10 from the surrounding ambient temperature with insulation 20 and quartz window 22, the temperature gradient $T_1 - T_2$ remains fixed and stable.

The wells 14, which make up array 15, preferably have a volume of 250 μl with the dimensions being about ¼" in diameter and 5/16" deep. Alternatively, the volume of wells 14 can be of various volumes or shapes. Wells 14 are coated with a chemically inert and optically reflective material having good thermal conductive properties. In the preferred embodiment, wells 14 are plated with a thin layer of gold. Alternatively, wells 14 can be coated with polytetrafluoroethylene. Additionally, wells 14 can consist of removable wells made of quartz, glass or polytetrafluoroethylene.

Array 15 is filled with a reactant solution using the following method. First, the top horizontal row of wells 14 is filled with reactant solution at a known pH level. Each well 14 is filled with a measured volume (250 μl) of reactant solution. For binding (intermolecular) reactions, a known amount of protein is titrated with varying amounts of a reactant agent across the row of wells 14 where the amount of reactant agent in each well 14 increases across the row. For an unfolding reaction (intramolecular reaction) no titrating is performed. Second, the row of wells directly below the top row is filled with a reactant solution at a different pH level than the top row. For binding (intermolecular) reactions, the reactant solution is titrated in the same manner as that in the top row. The process is repeated for each suceeding row where each horizontal row is filled with reactant solution at a different pH level. Alternatively, each row of wells 14 may contain a different chemical additive instead of having different pH levels. The reactants are mixed before being placed in wells 14, thus the need to stir reactant solutions in wells 14 is avoided along with the undesired heat effects due to stirring.

The 12×8 array 15 allows data to be collected in two dimensions for testing a reactant solution at eight different pH levels or with eight different chemical additives at twelve different temperatures. In two dimensional data collecting, each horizontal row of twelve wells 14 would be at a different pH level or have a different chemical additive included. Alternatively, the number of wells in the array may be increased or decreased.

In the preferred embodiment, fluorescence sensor 100 is located directly above array 15. Fiber optic device 104 is housed within fluorescence sensor 100 and two stepping motors (not shown) move fiber optic device 104 in a x-axis and a y-axis. Fiber optic device 104 moves over each well 14 of array 15 and measures the fluorescence intensity emitted by the reactant solution sample held in each well 14 after the equilibrium of the reaction has been attained. Fiber optic cable 106 connects fiber optic device 104 to fluorescence spectrometer 102. Fluorescence spectrometer 102 converts the fluorescence intensity read by fiber optic device 104 into digital data.

In the preferred embodiment the raw data from the fluorescence measurements is processed into a computer 110 (FIG. 1) which, using the above equations, computes the values for the heat of reaction ΔH and the degree of advancement of the reaction e. The apparatus and method of the present invention can determine the heat of reaction and equilibrium constant for both inter and intramolecular reactions at several different values of pH in about 1 hour. The same results would take 3 to 8 days using conventional methods.

Both intermolecular and intramolecular reactions often take place with a change in fluorescence intensity. For example, for an unfolding (intramolecular) reaction, the unfolding of a protein in a sample of reactant solution can be detected by sensing the corresponding change in fluorescence intensity emitted by the sample of reactant solution. Furthermore, for a binding (intermolecular) reaction, the binding of a reactant agent to a protein in a sample of reactant solution can be detected by sensing the corresponding change in fluoresence intensity. Fluorescence measurements are highly sensitive and only minute amounts of reactant materials are required. This translates into significant savings for situations where proteins must be isolated by costly purification methods.

Alternatively, the radiational intensity emitted by a sample reactant solution can be measured by means other than measuring fluorescence intensity such as by measuring radioactively labelled materials, measuring luminescence, measuring the absorption of ultraviolet radiation or measuring the absorption of visible radiation.

Figure 4:
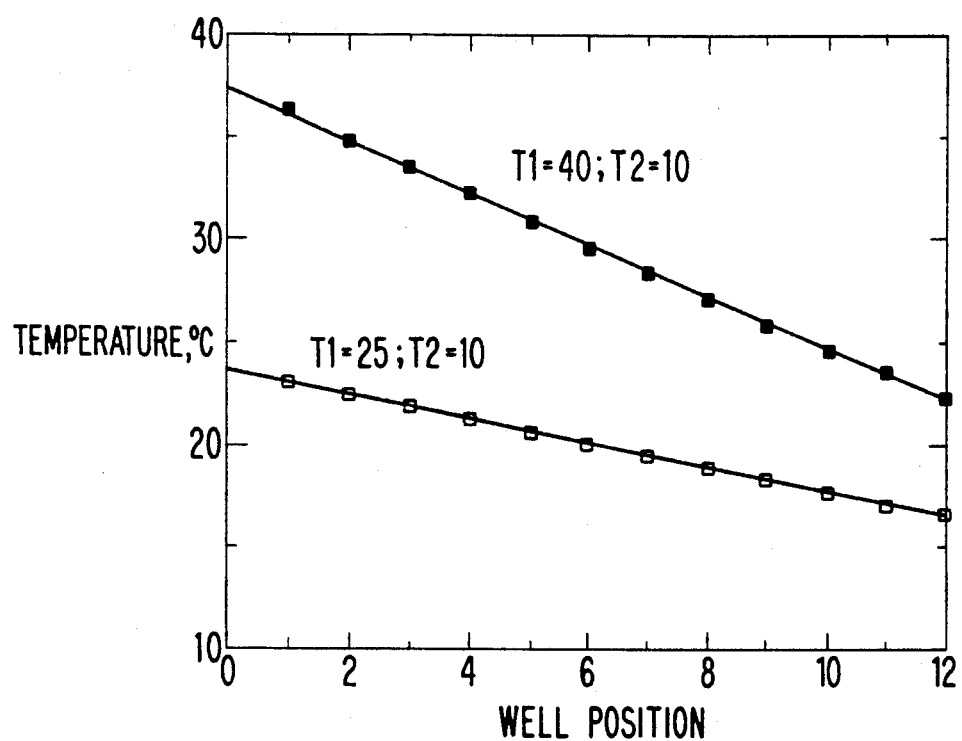
FIG. 4 illustrates the fluorescence intensity profile across the array of wells.
Figures 3A, 3B:
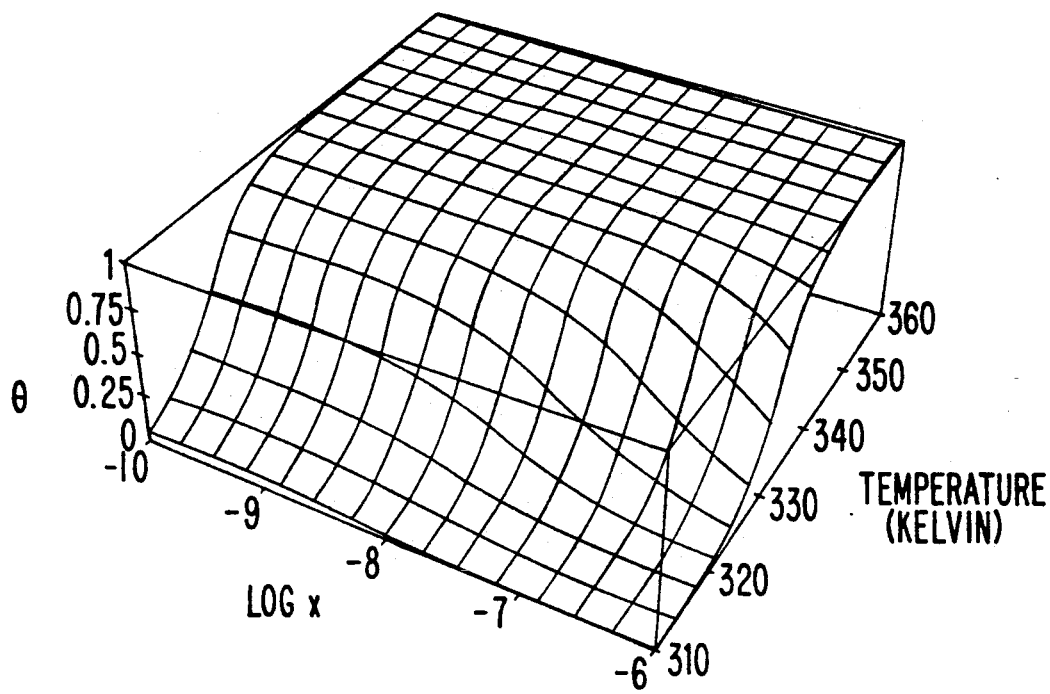
FIGS. 3a-3b are a graphs illustrating two different temperature gradient profiles across the array of wells.

The extent of reaction taking place in a given well 14 (FIG. 1) is dependent on temperature and concentration of an added agent. For example, in a binding (intermolecular) reaction, a different amount of protein will bind with a fixed amount of reactant agent at different temperatures. Therefore, the extent of reaction for a reactant solution varies across the x-direction of array 15 due to the temperature gradient across array 15 and varies across the y-direction due to a change in concentration of a reactant agent. FIG. 3a provides an example of a further representation of the extent of reaction of a drug with a protein as a function of temperature and concentration of the drug which binds to the protein. In the temperature gradient calorimeter 10 (FIG. 1), the concentration variation is achieved by mixing solutions before dispensing into the wells 14 of array 15. The temperature gradient is established as described above. FIG. 4 illustrates two examples of temperature gradients across array 15 (FIG. 1) as a function of well position on the x-axis. Due to the temperature gradient across array 15, each vertical column of eight wells 14 in the y-axis is at a different temperature than any of the other columns and each well 14 in a column is at the same temperature. FIG. 3b illustrates this change in the extent of reaction with a corresponding change in fluorescence intensity across array 15. Array 15 is identified in FIG. 3b by horizontal rows indicated as "a" through "h" and by vertical columns indicated as 1 through 12. The temperature gradient moves horizontally from vertical columns 1 through 12. The fluorescence intensity of the reactant solution held in array 15 varies with the change in temperature across array 15 and also with the change in concentration of a reactant agent vertically along array 15.

Once the fluorescence patterns of the reactant samples are measured, the heats of reactions can be determined by correlating reaction processes with differences in patterns of fluorescence intensity changes that occur due to a fixed temperature differential. Thermodynamic principles provide that the variation of the equilibrium constant with temperature is proportional to the heat of the reaction (also called the enthalpy of the reaction). This principle is summarized by the following mathematical expression:

$$\frac{d\ln K}{d\tau} = -\frac{\Delta H}{R} \quad [1]$$

where:
K is the equilibrium constant
$\tau$ is the reciprocal absolute temperature
$\Delta H$ is heat change for the reaction
R is the gas constant.

Equation (1) can be expressed in terms of $\Delta H$ where:

$$\Delta H = -R\frac{d\ln K}{d\tau} \quad [2]$$

The temperature gradient calorimetry method provides a measure of the heat of the reaction by providing the necessary information on the right hand side of equation [2], namely the variation of the equilibrium constant K with temperature.

The equilibrium constant K is also related to a quantity known as the degree of advancement of the reaction $\Theta$, which reflects the relative amount of a reaction mixture that has been converted to products.

Determining the heats of reaction for a binding (intermolecular) reaction and an unfolding (intramolecular) reaction requires the use of different sets of equations.

For a binding (intermolecular) reaction (M+X→MX), the equilibrium constant can be expressed in terms of the degree advancement of reaction $\Theta$ as:

$$K=\Theta/[(1-\Theta)x] \quad [3]$$

where x is the free (unreacted) concentration of the reactant X.

Substituting equation [3] into equation [2] results in:

$$\Delta H = \frac{-R\frac{d\theta}{d\tau}}{\theta(1-\theta)} + \frac{Rd\ln X}{d\tau} \quad [4]$$

The degree of advancement of the reaction at a fixed temperature column in the array can be expressed by:

$$\theta = \frac{\Delta F}{\Delta F_{total}} = \frac{K(T)x}{1+K(T)x} \quad [5]$$

where
$\Delta F$ is the change in fluorescence intensity from one well site to the next adjacent well site
$\Delta F_{total}$ is the total change in fluorescence intensity over a fixed temperature column
x is the free ligand concentration of X
K(T) is the equilibrium constant at a given temperature.

Figure 5:
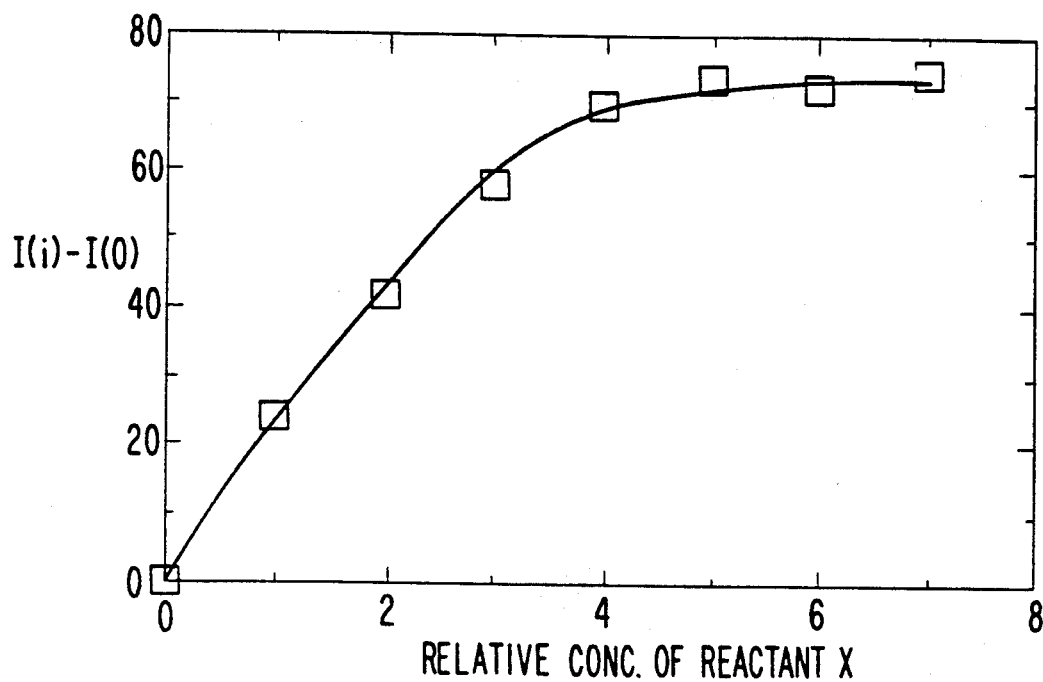
FIG. 5 is a graph showing an example of the change in fluorescence intensity for an binding (intermolecular) reaction.

Once the fluorescence intensity for a binding (intermolecular) reaction has been measured across array 15 (FIG. 1), the resulting data can be graphed. FIG. 5 is a graph depicting fluorescence intensity versus the relative amount of added reactant for a given fixed temperature column. A value of the equilibrium constant at that temperature, K(T), can be extracted from the data by equation (5), by considering that the free ligand concentration x is determined in the fit by the positive solution to:

$$Kx^2+(1+kM_T-kX_T)-X_T=0 \quad [6]$$

where $M_T$ and $X_T$ are the total concentrations of protein and ligand in the sample wells respectively. Values of $\Delta F_{total}$ and K(T) are determined in the fitting procedure. This procedure is carried out for each constant temperature column so that a set of K(T)'s at different temperatures are collected. Equation [2] is then used to compute the heat of the reaction, $\Delta H$.

Some of the equations used in determining the heats of reaction for an unfolding (intramolecular) reaction are different than those used for a binding (intermolecular) reaction. For an unfolding (intramolecular) reaction (M→M'), the equilibrium constant can be expressed in terms of the degree of advancement of a reaction as:

$$K=\Theta/(1-\Theta) \quad [7]$$

The substitution of equation [7] into equation [2] results in:

$$\Delta H = \frac{-R\frac{d\theta}{d\tau}}{\theta(1-\theta)} \quad [8]$$

Figure 6:
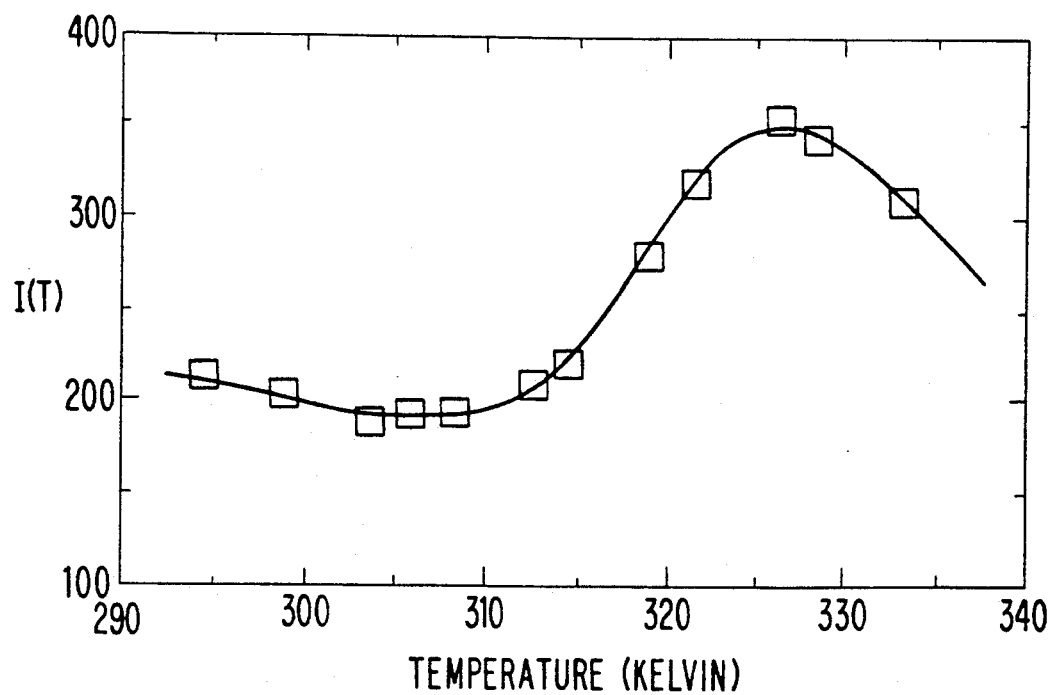
FIG. 6 is a graph showing an example of the change in fluorescence intensity monitored as a function of temperature for an unfolding (intramolecular) reaction.

FIG. 6 is a graph of raw data showing fluorescence intensity monitored as a function of temperature for a given horizontal row used in monitoring the unfolding of a protein. The curve of the data points shown in FIG. 6 is approximated by the equation:

$$I(T) = I_m(T) + [I_{m'}(T) - I_m(T)]\Theta \quad [9]$$

where:

$$I_{m'}(T) = a + bT \quad [10]$$

and $$I_m(T) = c + dT \quad [11]$$

The degree of advancement of the reaction can be expressed by:

$$\Theta = \frac{I(T) - I_m(T)}{I_{m'}(T) - I_m(T)} = \frac{e^{\frac{-\Delta H}{R}(\tau - \tau_m)}}{1 + e^{\frac{-\Delta H}{R}(\tau - \tau_m)}} \quad [12]$$

where $\tau$ is the reciprocal temperature in degrees Kelvin, and a, b, c, d, $\tau_M$ and $\Delta H$ are constants determined in the fitting procedure.

Figure 7:
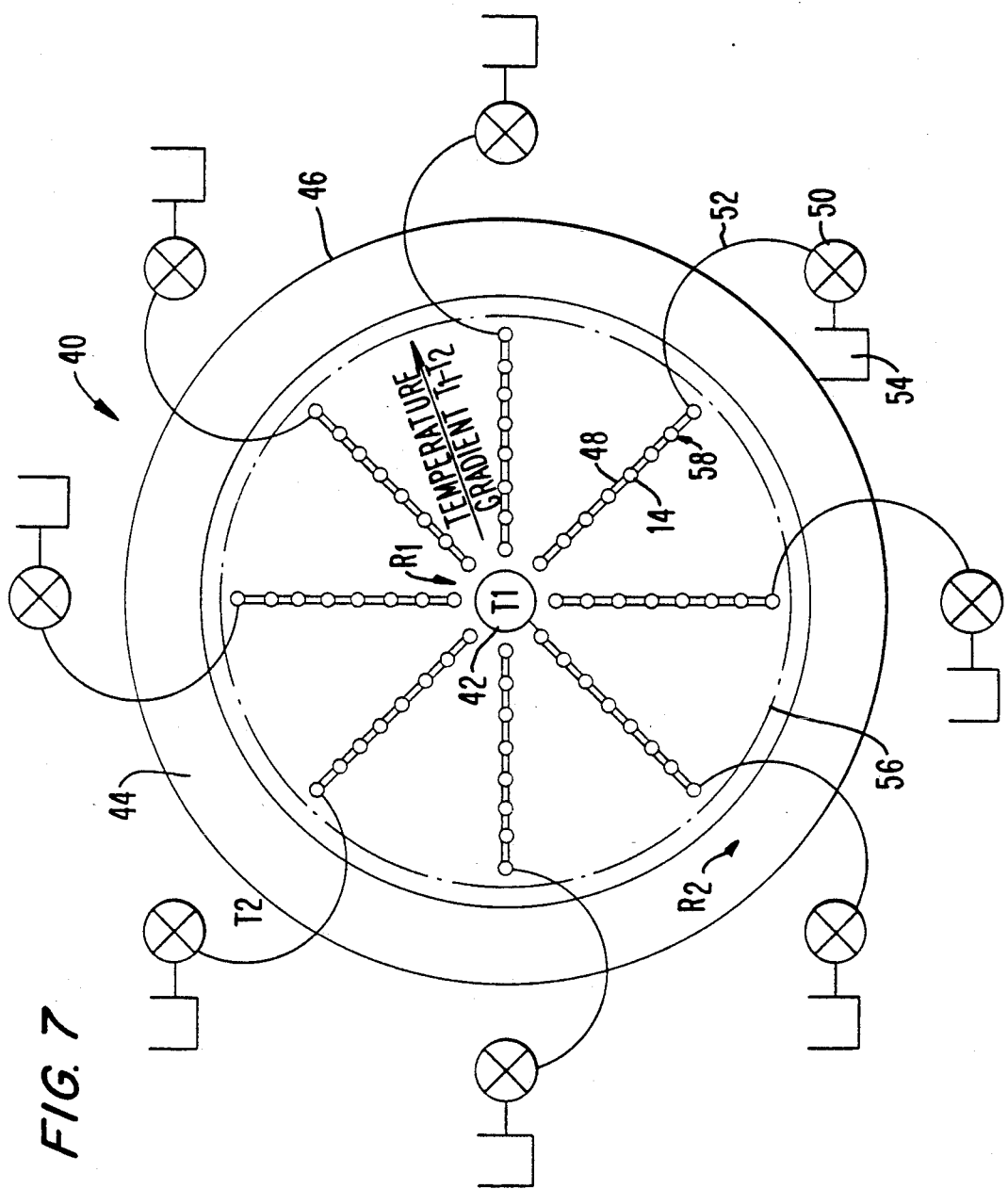
FIG. 7 is plan view of a temperature gradient calorimeter having a coaxial temperature gradient and a series of connecting canals for filling wells.

An alternative embodiment of the present invention is shown in FIG. 7 where temperature gradient calorimeter 40 is circular rather than rectangular. Flow tube 42, maintained at temperature $T_1$, is in thermal contact with region $R_1$ at the center of substrate 46. Flow tube 44, maintained at temperature $T_2$ is in thermal contact with region $R_2$ at the outer edge of substrate 46. The difference in temperature $T_1$-$T_2$ between flow tube 42 at region $R_1$ and flow tube 44 at region $R_2$ produces a radial temperature gradient between regions $R_1$ and $R_2$.

Rho/theta array 56 of wells 14 is located within the temperature gradient between regions $R_1$ and $R_2$. Array 56 is made up of a number of equally spaced rows 58 of wells 14 extending radially outward from $R_1$ across the temperature gradient towards region $R_2$. Valves 50 permits a measured amount of reactant solution from reservoir 54 to enter canals 48 via trough 52. Canals 48 connect each well 14 of a row 58. Canals 48 allow an entire row 58 of wells 14 to be filled at the same time with reactant solution.

FIG. 8 shows an alternative embodiment of the present invention where temperature gradient calorimeter 60 maintains a constant protein concentration in sample well 14, but changes the concentration (in sample well 14) of an agent which binds to it, such as the binding of oxygen to hemoglobin or whole blood. This is made possible by environment chamber 66 which exchanges gases between sample wells 14 and environment chamber 66 through membrane 64, where environment chamber 66 is a gas phase dialysate chamber and membrane 64 is a gas-permeable membrane. Sample wells 14 pass through substrate 68 so that membrane 64 makes up the bottom of sample wells 14, separating wells 14 from environment chamber 66. Sample window 62 covers the top of sample wells 14. Alternatively, environment chamber 66 can be a liquid dialysate chamber and membrane 64 can be a semi-permeable membrane allowing liquids rather than gases to pass from environment chamber 66 to wells 14.

FIG. 9 shows a segmented temperature gradient calorimeter 70. In this alternative embodiment of the present invention, a number of individual substrates 72 make up calorimeter 70. Each individual substrate 72 contains a vertical column 74 of wells 14 and is individually cooled or heated. The individual substrates 72 are thermally isolated from each other by an insulating material. The temperature of each adjacent substrate 72 can be in ascending or descending temperature so that the overall effect is a stepped temperature gradient over calorimeter 70.

While this invention has been particularly shown and described with references to preferred embodiment thereof, it will be understood by those skilled in the art that various changes in form and details may be made therein without departing from the spirit and scope of the invention as defined by the appended claims.

I claim:

1. Apparatus for monitoring reactions comprising:
   (a) a two dimensional array of reaction chambers formed in a heat conductive substrate;
   (b) a first heat transfer medium at a temperature $T_1$ in thermal contact with a first region of said substrate;
   (c) a second heat transfer medium at a constant temperature $T_2$ in thermal contact with a second region of said substrate; whereby a thermal gradient is established across said array and between said first and second regions which is proportional to the difference in temperature, $T_1$-$T_2$, between the two mediums.

2. The apparatus of claim 1 including a sensor for sensing radiation intensity emitted from each chamber as a reaction occurs.

3. The apparatus of claim 2 where the intensity of radiation emitted from each chamber is measured with a sensor belonging to the group comprising a sensor for measuring the intensity of fluorescence resulting, a sensor for measuring radioactive labelled materials, a sensor for measuring the absorption of ultraviolet radiation and a sensor for measuring the absorption of visible radiation.

4. The apparatus of claim 1 further comprising a dialysate chamber which is separated from the reaction chambers by a semi-permeable membrane.

5. The apparatus of claim 1 further comprising a transparent window covering the array of reaction chambers.

6. The apparatus of claim 1 where the heat conductive substrate is substantially enclosed within an insulating material.

7. The apparatus of claim 1 including a filling system for filling the array of reaction chambers comprising a series of canals connecting a plurality of reaction chambers.

8. The apparatus of claim 1 where the first and second heat transfer mediums comprise temperature controlled water baths.

9. The apparatus of claim 1 where the reaction chambers are coated with a chemically inert and optically reflective material having good thermal conductive properties.

10. The apparatus of claim 1 where the heat conductive substrate is made from a metallic material from the group comprising saphire, silicon, copper, aluminum or stainless steel.

11. The apparatus of claim 1 in which the reaction involve temperature changes.

12. The apparatus of claim 1 in which the reactions are chemical reactions.

13. The apparatus of claim 1 in which the thermal gradient is a fixed temperature gradient.

14. A temperature gradient calorimeter comprising:
   a) a two dimensional array of reaction chambers arranged in a substrate and wherein a constant thermal gradient is established across the array;
   b) a sensor for measuring the intensity of radiation emitted by reactions occurring in the reaction chambers in which intensity varies in proportion to the thermal gradient.

15. The temperature gradient calorimeter of claim 14 where the sensor measures fluorescence intensity emitted by reactions occurring in the reaction chambers.

16. A method of monitoring reactions comprising:
   creating a constant temperature gradient across a two dimensional array of reaction chambers disposed in a heat conductive substrate;
   measuring the intensity of radiation emitted from the reactant solution in each reaction chamber across the array of reaction chambers;
   determining the heat of reaction for each reaction from the measured intensities of the reaction in each chamber.

17. The method of monitoring reactions of claim 16 including the step of connecting the reaction chambers in each row with a canal and filling each canal with reactant solution, each canal carrying reactant solution to a row of reaction chambers, thereby filling each reaction chamber.

18. The method of monitoring reactions of claim 16 where the step of creating a temperature gradient across the array of reaction chambers comprises placing a first heat transfer medium at a temperature $T_1$ in thermal contact with a first region of the heat conductive substrate; and by placing a second heat transfer medium at a temperature $T_2$ in thermal contact with a second region of the heat conductive substrate.

19. The method of monitoring reactions of claim 13 where the radiation intensity measured emitted from the reactant solution in each reaction chamber is fluorescence intensity.

20. The method of monitoring reactions of claim 13 where the step of determining the heat of reaction for the reactant solution includes correlating fluorescence intensity data with thermodynamic expressions of heat of reaction and degree of advancement of reaction.

21. The method of monitoring reactions of claim 17 where the step of determining the heat of reaction for the reactant solution further includes using a computer for computing the heat of reaction and the degree of advancement of reaction.

22. The method of monitoring reactions of claim 16 in which the reactions involve temperature changes.

23. The method of monitoring reactions of claim 16 in which the reactions are chemical reactions.

24. A temperature gradient calorimeter comprising:
   a) a two dimensional array of reaction chambers formed in a heat conductive substrate, said reaction chambers in the two dimensional array being arranged in horizontal rows on the x-axis and vertical columns on the y-axis;
   b) a first heat flow medium at a temperature $T_1$ in thermal contact with a first region of said substrate;
   c) a second heat flow medium at a constant temperature $T_2$ in thermal contact with a second region of said substrate; whereby a thermal gradient is established between said first and second regions which is proportional to the difference in temperature, $T_1-T_2$, between the two mediums;
   d) a sensor for measuring the fluorescence intensity emitted by reactions occurring in the reaction chambers in which intensity varies in proportion to the thermal gradient.

* * * * *

UNITED STATES PATENT AND TRADEMARK OFFICE
CERTIFICATE OF CORRECTION

PATENT NO. : 5,255,976

DATED : October 26, 1993

INVENTOR(S) : Patrick R. Connelly

It is certified that error appears in the above-identified patent and that said Letters Patent is hereby corrected as shown below:

| Column | Line | |
|---|---|---|
| 1 | 14 | "interriolecular" should be --intermolecular--. |
| 4 | 39 | "e" should be --θ--. |
| 5 | 51 | "$\pi$" should be --$\tau$--. |
| 6 | 17 | In Equation 4, "Rdlnx" should be --Rdlnx--. |
| 6 | 44 | In Equation 6, capitalize "k" in the second and third occurrences. |
| 7 | 7 | "$I(T)=I_m(T)+[I_m(T)-I_m(T)\theta$" should be --$I(T)=I_m(T)+[I_m'(T)-I_m(T)]\theta$--. |
| 7 | 14 | "$I_m(T)=c+dT$" should be --$I_m'(T)=c+dT$--. |

UNITED STATES PATENT AND TRADEMARK OFFICE
CERTIFICATE OF CORRECTION

PATENT NO. : 5,255,976

DATED : October 26, 1993

INVENTOR(S) : Patrick R. Connelly

It is certified that error appears in the above-identified patent and that said Letters Patent is hereby corrected as shown below:

| Column | Line | |
|---|---|---|
| 7 | 20 | In Equation 12, both occurrences of "$(\tau-\tau m)$" should be --$(\tau-\tau_m)$--. |
| 8 | 63 | "reaction" should be --reactions--. |
| 7 | 34 | "f low" should be --flow--. |

Signed and Sealed this

Eighth Day of November, 1994

Attest:

BRUCE LEHMAN

Attesting Officer

Commissioner of Patents and Trademarks